US006499366B1

(12) United States Patent
Meadows et al.

(10) Patent No.: US 6,499,366 B1
(45) Date of Patent: Dec. 31, 2002

(54) SAMPLE FEEDER

(75) Inventors: John W. Meadows, Los Altos Hills, CA (US); Glenn R. Edwards, Palo Alto, CA (US); Samuel A. Marquiss, Santa Clara, CA (US); Amer El-Hage, Menlo Park, CA (US); Douglas N. Modlin, Palo Alto, CA (US)

(73) Assignee: LJL BioSystems, Inc., Sunnyvale, CA (US)

( * ) Notice: Subject to any disclaimer, the term of this patent is extended or adjusted under 35 U.S.C. 154(b) by 0 days.

(21) Appl. No.: 09/144,578

(22) Filed: Aug. 31, 1998

Related U.S. Application Data

(63) Continuation of application No. 09/062,472, filed on Apr. 17, 1998, now Pat. No. 6,071,748, and a continuation of application No. PCT/US98/14575, filed on Jul. 15, 1998, now abandoned, and a continuation of application No. 09/118,141, filed on Jul. 16, 1998, now Pat. No. 6,313,960, and a continuation of application No. 09/118,310, filed on Jul. 16, 1998, now Pat. No. 6,033,100, and a continuation of application No. 09/118,341, filed on Jul. 16, 1998, now Pat. No. 6,025,985.

(60) Provisional application No. 60/052,876, filed on Jul. 16, 1997, provisional application No. 60/059,639, filed on Sep. 20, 1997, provisional application No. 60/063,811, filed on Oct. 31, 1997, provisional application No. 60/072,499, filed on Jan. 26, 1998, provisional application No. 60/072,780, filed on Jan. 27, 1998, provisional application No. 60/075,414, filed on Feb. 20, 1998, provisional application No. 60/075,806, filed on Feb. 24, 1998, provisional application No. 60/082,253, filed on Apr. 17, 1998, provisional application No. 60/084,167, filed on May 4, 1998, provisional application No. 60/085,335, filed on May 13, 1998, provisional application No. 60/085,500, filed on May 14, 1998, provisional application No. 60/089,848, filed on Jun. 19, 1998, provisional application No. 60/094,275, filed on Jul. 27, 1998, provisional application No. 60/094,276, filed on Jul. 27, 1998, and provisional application No. 60/094,306, filed on Jul. 27, 1998.

(51) Int. Cl.[7] .......................... G01N 35/04; G01N 35/10
(52) U.S. Cl. ...................................... 73/864.81; 422/63
(58) Field of Search .......................... 73/864.81, 865.8; 422/63, 65

(56) References Cited

U.S. PATENT DOCUMENTS 2,719,214 A  9/1955  Potter
3,013,467 A  12/1961 Minsky (List continued on next page.)

FOREIGN PATENT DOCUMENTS

EP  0 266 881 A2  5/1988
EP  0 259 386 A1  4/1991

(List continued on next page.)

OTHER PUBLICATIONS

Electrochemiluminescence: A New Diagnostic and Research Tool, Yang et al., *Bio/Technology*, vol. 12, pp. 193–194, Feb. 1994.

(List continued on next page.)

*Primary Examiner*—Hezron Williams
*Assistant Examiner*—Rose M. Miller
(74) *Attorney, Agent, or Firm*—Kolisch Hartwell, P.C.

(57) ABSTRACT

Devices for automatically feeding sample containers into and out of an analyzer. The device may include (1) a first station that receives and initiates transport of a sample container into an analyzer for analysis, (2) a second station where the sample container is handed off to a transporter that carries the sample container to and from an examination site inside the analyzer, and (3) a third station that collects the sample container after examination. The device also may include a singulation mechanism configured to separate a sample container from a stack of sample containers, and/or a stacking mechanism configured to add a sample container to a stack of sample containers. The singulation and stacking mechanisms may include lifter and latch components.

27 Claims, 8 Drawing Sheets

U.S. PATENT DOCUMENTS

| | | |
|---|---|---|
| 3,423,581 A | 1/1969 | Baer |
| 3,516,736 A | 6/1970 | Weaver |
| 3,849,654 A | 11/1974 | Malvin |
| 3,932,023 A | 1/1976 | Humer |
| 4,011,451 A | 3/1977 | Nelson |
| 4,067,653 A | 1/1978 | Fletcher et al. |
| 4,076,420 A | 2/1978 | De Maeyer et al. |
| 4,100,416 A | 7/1978 | Hirschfeld |
| 4,144,452 A | 3/1979 | Harte |
| 4,150,870 A | 4/1979 | d'Auria |
| 4,203,670 A | 5/1980 | Bromberg |
| 4,240,751 A | 12/1980 | Linnecke et al. |
| 4,296,326 A | 10/1981 | Haslop et al. |
| 4,341,957 A | 7/1982 | Wieder |
| 4,451,149 A | 5/1984 | Noeller |
| 4,485,430 A | 11/1984 | Achiaga Fustel |
| 4,501,970 A | 2/1985 | Nelson |
| 4,567,847 A | 2/1986 | Linner |
| 4,626,684 A | 12/1986 | Landa |
| 4,646,214 A | 2/1987 | Mendleski |
| 4,685,801 A | 8/1987 | Minekane |
| 4,699,512 A | 10/1987 | Koshi |
| 4,704,255 A | 11/1987 | Jolley |
| 4,704,353 A | 11/1987 | Humphries et al. |
| 4,707,067 A | 11/1987 | Haberland et al. |
| 4,724,217 A | 2/1988 | Miller |
| 4,730,921 A | 3/1988 | Klein et al. |
| 4,738,825 A | 4/1988 | Kelln et al. |
| 4,741,619 A | 5/1988 | Humphries |
| 4,753,501 A | 6/1988 | Battle |
| 4,762,420 A | 8/1988 | Bowley |
| 4,772,453 A | 9/1988 | Lisenbee |
| 4,784,275 A | 11/1988 | Fridge |
| 4,801,804 A | 1/1989 | Rosenthal |
| 4,810,096 A | 3/1989 | Russell et al. |
| 4,826,660 A | 5/1989 | Smith et al. |
| 4,855,930 A | 8/1989 | Chao et al. |
| 4,861,554 A * | 8/1989 | Sakuma ............... 422/65 |
| 4,868,103 A | 9/1989 | Stavrianopoulos et al. |
| 4,873,633 A | 10/1989 | Mezei et al. |
| 4,877,965 A | 10/1989 | Dandliker et al. |
| 4,885,087 A | 12/1989 | Kopf |
| 4,892,409 A | 1/1990 | Smith |
| 4,897,548 A | 1/1990 | Döme et al. |
| 4,923,819 A | 5/1990 | Fernandez et al. |
| 4,931,402 A | 6/1990 | Abplanalp |
| 4,936,682 A | 6/1990 | Hoyt |
| 4,948,442 A | 8/1990 | Manns |
| 4,968,148 A | 11/1990 | Chow et al. |
| 4,979,821 A | 12/1990 | Schutt et al. |
| 5,009,488 A | 4/1991 | Fay et al. |
| 5,034,613 A | 7/1991 | Denk et al. |
| 5,039,219 A | 8/1991 | James et al. |
| 5,047,215 A | 9/1991 | Manns |
| 5,058,045 A | 10/1991 | Ma |
| 5,082,628 A | 1/1992 | Andreotti et al. |
| 5,084,246 A | 1/1992 | Lyman et al. |
| 5,091,652 A | 2/1992 | Mathies et al. |
| 5,095,517 A | 3/1992 | Monguzzi et al. |
| 5,096,807 A | 3/1992 | Leaback |
| 5,169,601 A | 12/1992 | Ohta et al. |
| 5,192,510 A | 3/1993 | Zoha et al. |
| 5,198,670 A | 3/1993 | VanCauter et al. |
| 5,206,568 A | 4/1993 | Bjornson et al. |
| 5,208,161 A | 5/1993 | Saunders et al. |
| 5,208,651 A | 5/1993 | Buican |
| 5,216,488 A | 6/1993 | Tuunanen et al. |
| 5,225,164 A | 7/1993 | Astle |
| 5,257,202 A | 10/1993 | Feddersen et al. |
| 5,270,788 A | 12/1993 | Cercek et al. |
| 5,273,718 A | 12/1993 | Sköld et al. |
| 5,275,951 A | 1/1994 | Chow et al. |
| 5,289,407 A | 2/1994 | Strickler et al. |
| 5,307,144 A | 4/1994 | Hiroshi et al. |
| 5,315,015 A | 5/1994 | Hui et al. |
| 5,317,485 A | 5/1994 | Merjanian |
| 5,319,436 A | 6/1994 | Manns et al. |
| 5,323,008 A | 6/1994 | Studholme et al. |
| 5,340,716 A | 8/1994 | Ullman et al. |
| 5,340,747 A | 8/1994 | Eden |
| 5,341,215 A | 8/1994 | Seher |
| 5,353,112 A | 10/1994 | Smith |
| 5,355,215 A | 10/1994 | Schroeder et al. |
| 5,361,626 A | 11/1994 | Colligan et al. |
| 5,384,093 A | 1/1995 | Ootani et al. |
| 5,401,465 A | 3/1995 | Smethers et al. |
| 5,418,371 A | 5/1995 | Aslund et al. |
| 5,420,408 A | 5/1995 | Weyrauch et al. |
| 5,436,718 A | 7/1995 | Fernandes et al. |
| 5,445,935 A | 8/1995 | Royer |
| 5,449,921 A | 9/1995 | Baba |
| 5,457,527 A | 10/1995 | Manns et al. |
| 5,459,300 A | 10/1995 | Kasman |
| 5,480,804 A | 1/1996 | Niwa et al. |
| 5,485,530 A | 1/1996 | Lakowicz et al. |
| 5,487,872 A | 1/1996 | Hafeman et al. |
| 5,491,343 A | 2/1996 | Brooker |
| 5,512,492 A | 4/1996 | Herron et al. |
| 5,523,573 A | 6/1996 | Hänninen et al. |
| 5,527,684 A | 6/1996 | Mabile et al. |
| 5,528,046 A | 6/1996 | Ishikawa |
| 5,528,146 A | 6/1996 | Ishikawa |
| 5,537,343 A | 7/1996 | Kikinis et al. |
| 5,541,113 A | 7/1996 | Siddigi et al. |
| 5,542,012 A | 7/1996 | Fernandes et al. |
| 5,557,398 A | 9/1996 | Wechsler et al. |
| 5,589,136 A | 12/1996 | Northrup et al. |
| 5,589,350 A | 12/1996 | Bochner |
| 5,589,351 A | 12/1996 | Harootunian |
| 5,592,289 A | 1/1997 | Norris |
| 5,593,867 A | 1/1997 | Walker et al. |
| 5,595,710 A | 1/1997 | Van Dusen et al. |
| 5,599,500 A | 2/1997 | Jones |
| 5,604,130 A | 2/1997 | Warner et al. |
| 5,610,683 A * | 3/1997 | Takahashi ............... 355/53 |
| 5,620,894 A | 4/1997 | Barger et al. |
| 5,626,134 A | 5/1997 | Zuckerman |
| 5,631,734 A | 5/1997 | Stern et al. |
| 5,633,724 A | 5/1997 | King et al. |
| 5,635,402 A | 6/1997 | Alfano et al. |
| 5,641,633 A | 6/1997 | Linn et al. |
| 5,645,800 A | 7/1997 | Masterson et al. |
| 5,663,545 A | 9/1997 | Marquiss |
| 5,670,113 A | 9/1997 | Akong et al. |
| 5,672,880 A | 9/1997 | Kain |
| 5,676,943 A | 10/1997 | Baetge et al. |
| 5,677,196 A | 10/1997 | Herron et al. |
| 5,679,310 A | 10/1997 | Manns |
| 5,736,410 A | 4/1998 | Zarling et al. |
| 5,738,825 A | 4/1998 | Rudigier et al. |
| 5,746,974 A | 5/1998 | Massey et al. |
| 5,750,410 A | 5/1998 | Dou et al. |
| 5,756,292 A | 5/1998 | Royer |
| 5,780,857 A | 7/1998 | Harju et al. |
| 5,798,083 A | 8/1998 | Massey et al. |
| 5,798,085 A | 8/1998 | Seaton et al. |
| 5,825,617 A | 10/1998 | Kochis et al. |
| 5,842,582 A | 12/1998 | DeStefano, Jr. |
| 5,888,454 A | 3/1999 | Leistner et al. |
| 5,933,232 A | 8/1999 | Atzler et al. |
| 5,989,835 A | 11/1999 | Dunlay et al. |

| | | | |
|---|---|---|---|
| 5,993,746 A | 11/1999 | Priha et al. | |
| 6,020,591 A | 2/2000 | Harter et al. | |
| 6,025,985 A | 2/2000 | Leytes et al. | |
| 6,033,100 A | 3/2000 | Marquiss et al. | |
| 6,071,748 A | 6/2000 | Modlin et al. | |

FOREIGN PATENT DOCUMENTS

| | | |
|---|---|---|
| EP | 0 977 037 A1 | 2/2000 |
| EP | 0 993 916 A2 | 4/2000 |
| EP | 0 995 555 A1 | 4/2000 |
| EP | 1 003 020 A1 | 5/2000 |
| EP | 1 003 039 A1 | 5/2000 |
| GB | 2 215 838 A | 9/1989 |
| GB | 2 228 081 A | 8/1990 |
| JP | 102161 * | 6/1983 |
| JP | 296784 * | 5/1996 |
| JP | 236607 * | 9/1997 |
| JP | 89559 * | 4/1999 |
| JP | 121577 * | 4/1999 |
| WO | WO 99/08233 | 2/1999 |
| WO | WO 00/50877 | 8/2000 |
| WO | WO 00/55372 | 9/2000 |
| WO | WO00/66269 | 11/2000 |

OTHER PUBLICATIONS

High Throughput Screening Using Dynamic Fluorescence, Swift et al., *SPIE*, vol. 2388, pp. 182–189, Feb. 6–8, 1995.
Genesis Series Robotic Sample Processors brochure, Tecan AG, Nov. 1997.
Genesis Robotic Microplate Processor brochure, Tecan AG, Nov. 1997.
A Measure of Brilliance, TR717 Microplate Luminometer brochure, Tropix, Inc., 1997.
Advanced Microplate Detection Systems brochure, Tecan AG, Feb. 1998.
The Spectra Family brochure, Tecan AG, Feb. 1998.
Assist Plate Handling Device brochure, Labsystems, May 1998.
Genesis Assay Workstation brochure, Tecan AG, Jul. 1998.
Genesis Logistics Workstation brochure, Tecan AG, Jul. 1998.
Polarion brochure, Tecan AG, Aug. 1998.
Fixed Polarizer Ellipsometry for Single and Sensitive Detection of Thin Films Generated by Specific Molecular Interactions: Applications in Immunoassays and DNA Sequence Detection, Ostroff et al., *Clinical Chemistry*, vol. 44, No. 9, pp. 2031–2035, 1998.
CytoFluor Fluorescence Multi–Well Plate Reader brochure, PerSeptive Biosystems, 1998.
Microplate Instrumentation Catalogue 1998, Labsystems, 1998.
*Fundamentals of Light Microscopy*, Spencer, Cambridge University Press, 1982.
*Basic Fluorescence Microscopy*, Taylor et al., *Methods in Cell Biology*, vol. 29, pp. 207–237, 1989.
Quantitative Fluorescence Microscopy Using Photomultiplier Tubes and Imaging Detectors, Wampler et al., *Methods in Cell Biology*, vol. 29, pp. 239–267, 1989.
Three–Dimensional Confocal Fluorescence Microscopy, Brakenhoff, et al., *Methods in Cell Biology*, vol. 30, pp. 379–389, 1989.
Laser Scanning Confocal Microscopy of Living Cells, Lemasters et al., *Optical Microscopy: Emerging Methods and Applications*, pp. 339–345, 1993.
Time–Resolved Fluorescence Lifetime Imaging, vandeVen et al., *Optical Microscopy: Emerging Methods and Applications*, pp. 373–389, 1993.
Tecan Spectrafluor—A Step Forward in Microplate Fluorometry, internet description pages, printed from internet on Jun. 17, 1998.
Wallac Time–Resolved Fluorometry—The Key to Improved Assay Sensitivity, internet description pages, printed from internet on Jul. 7, 1998.
Wallac 1234 Delfia Fluorometer, internet description page, printed from internet on Jul. 7, 1998.
Wallac 1420 Victor Multilabel Counter, internet description pages, printed from internet on Jul. 7, 1998.
Wallac 1420 Victor$^2$ Multilabel Counter, internet description pages, printed from internet on Jul. 7, 1998.
Wallac 1442 Arthur Multi–Wavelength Fluoroimager, internet description page, printed form internet on Jul. 7, 1998.
Wallac Labelling Reagents for Time–Resolved Fluorometry, internet description page, printed from internet on Jul. 7, 1998.
LUMIstar Galaxy brochure, BMG Labtechnologies GmbH, undated.
NEPHELOstar brochure, BMG Labtechnologies GmbH, undated.
Polarstar Galaxy brochure, BMG Labtechnologies GmbH, undated.
Polarstar Galaxy flyer, BMG Labtechnologies, GmbH, undated.
Twister™, Tecan'Automated Microplate Handler brochure, Tecan AG, Nov. 1999.
Magellan, Instrument Control and Data Analysis Software brochure, Tecan AG, Nov. 1999.
Absorbance Readers brochure, Tecan AG, Dec. 1999.
Ultra—The Solution for HTS and Assay Development brochure, Tecan Austria GmbH, Dec. 1999.
CyBi™–Lumax 1,536 brochure, CyBio AG, May 2000.
Packard BioScience Company Introduces the Fusion™ Universal Microplate Analyzer press release, Packard BioScience Company, Jun. 29, 2000.
Spectramax® Gemini XS brochure, Molecular Devices Corp., Jun. 2000.
Spectramax® Plus$^{384}$ brochure, Molecular Devices Corp., Jun. 2000.
Labcyte: Research and Clinical Instruments for Life Sciences brochure, Arlean Research LLC, Aug. 1, 2000.
Fusion™, Universal Microplate Analyzer, Packard BioScience Company, Aug. 2000.
CyBi™–Screen–Machine: One System–Many Solutions brochure, CyBio AG, 2000.
FLIPR 384: Esseential Technology for Drug Discovery brochure, Molecular Devices Corp., undated.
Acumen Explorer brochure, Acumen, undated.
FLUOstar Galaxy brochure, BMG Labtechnologies GmbH, undated.

* cited by examiner

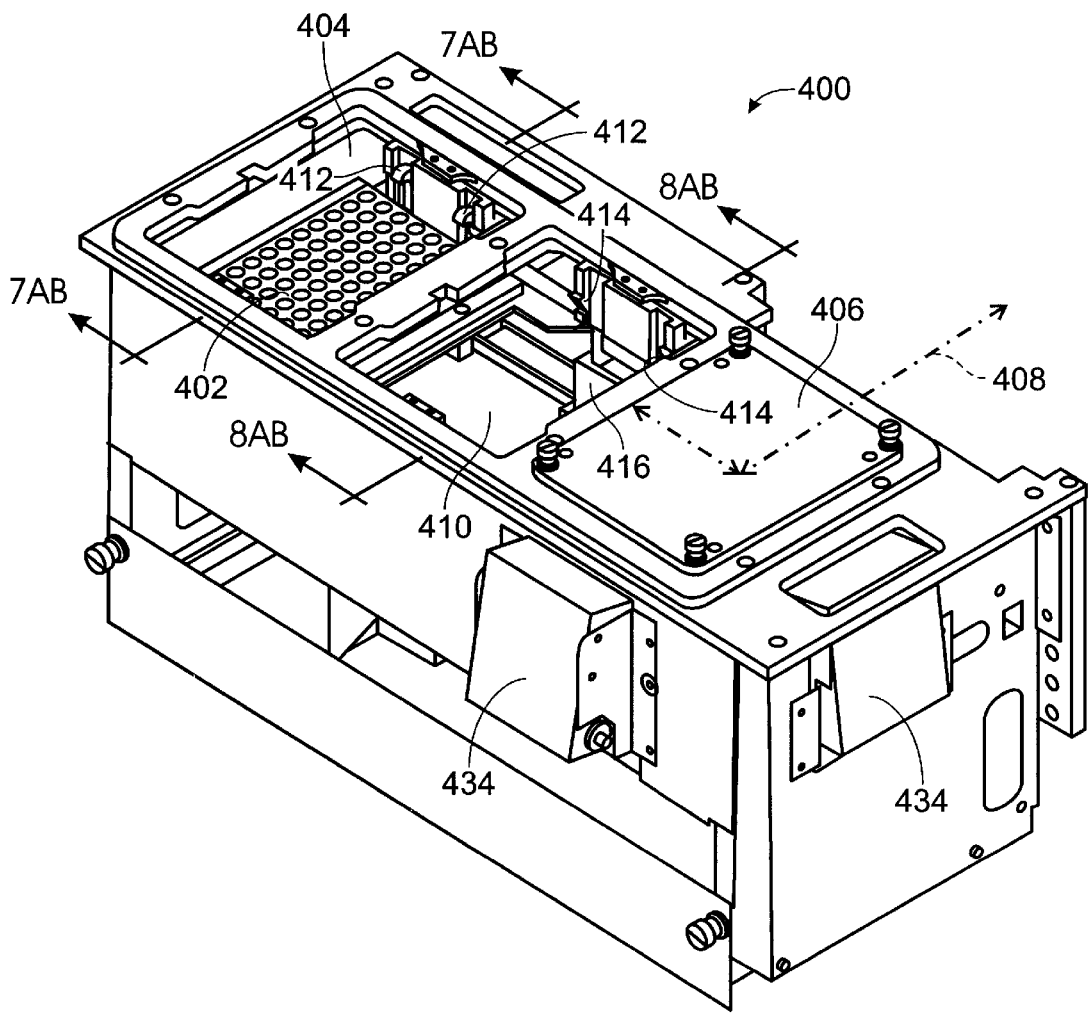

SAMPLE FEEDER

CROSS-REFERENCES TO RELATED APPLICATIONS

This application is a continuation of the following patent applications, each of which is incorporated herein by reference: U.S. patent application Ser. No. 09/062,472, filed Apr. 17, 1998, now U.S. Pat. No. 6,071,748; PCT Patent Application Ser. No. PCT/US98/14575, filed Jul. 15, 1998, now abandoned; U.S. patent application Ser. No. 09/118,141, filed Jul. 16, 1998, now U.S. Pat. No. 6,313,960; U.S. patent application Ser. No. 09/118,310, filed Jul. 16, 1998, now U.S. Pat. No. 6,033,100; and U.S. patent application Ser. No. 09/118,341, filed Jul. 16, 1998, now U.S. Pat. No. 6,025,985.

This application, directly and/or through its parent applications, is based upon and claims benefit under 35 U.S.C. §119 of the following U.S. Provisional Patent Applications, each of which is incorporated herein by reference: Ser. No. 60/052,876, filed Jul. 16, 1997; Ser. No. 60/059,639, filed Sep. 20, 1997; Ser. No. 60/063,811, filed Oct. 31, 1997; Ser. No. 60/072,499, filed Jan. 26, 1998; Ser. No. 60/072,780, filed Jan. 27, 1998; Ser. No. 60/075,414, filed Feb. 20, 1998; Ser. No. 60/075,806, filed Feb. 24, 1998; Ser. No. 60/082,253, filed Apr. 17, 1998; Ser. No. 60/084,167, filed May 4, 1998; Ser. No. 60/085,335, filed May 13, 1998; Ser. No. 60/085,500, filed May 14, 1998; Ser. No. 60/089,848, filed Jun. 19, 1998; Ser. No. 60/094,275, filed Jul. 27, 1998; Ser. No. 60/094,276, filed Jul. 27, 1998; and Ser. No. 60/094,306, filed Jul. 27, 1998.

This application incorporates by reference the following U.S. patent application Ser. No. 09/144,575, filed Aug. 31, 1998, now U.S. Pat. No. 6,159,425.

FIELD OF THE INVENTION

The invention relates to a device for high-throughput screening. More particularly, the invention relates to a device for automatically feeding microplates into an analyzer for high-throughput screening.

BACKGROUND OF THE INVENTION

High-throughput screening instruments (or analyzers) are critical tools in the pharmaceutical research industry and in the process of discovering and developing new drugs. High-throughput analyzers are used to assess the efficacy of candidate drug compounds. Dramatic increases in the number of these compounds and in the number of targets against which they may be directed have created a bottleneck in the development of new drugs and a need for analyzers that can operate with a high degree of analytical flexibility and speed. Analytical flexibility and speed are necessary because high-throughput applications may involve repeating the same operations hundreds of thousands of times, greatly magnifying even the smallest shortcomings.

One way to increase speed and analytical flexibility is to house a variety of small-volume samples in a single container. Toward this end, high-density containers known as microplates have been developed. Microplates are generally rectangular containers that include a plurality of sample wells for holding a plurality of samples. Microplates enhance speed by reducing transit time between samples and reduce cost by employing small amounts of reagents. Unfortunately, microplates also have a number of shortcomings. For example, microplates do not conform to any exact standard, so that their size, shape, and construction materials may vary, depending on vendor or batch. In addition, microplates may vary from opaque to transparent, so that analytical approaches developed for some microplates will not work for other microplates. Moreover, preferred microplates may differ, depending on application. Furthermore, microplates may allot only a small volume for each sample, so that signal is reduced and sample is more easily spilled during transit.

Another way to increase speed and analytical flexibility is to use robots and other devices to automate high-throughput screening procedures. For example, robots permit analyzers to run 24 hours a day. Unfortunately, current robotic systems have a number of shortcomings. For example, robots commonly are used to deliver samples to an analyzer for analysis. However, the robot typically must make separate trips to drop off a sample container, such as a microplate, before analysis, to retrieve the sample container after analysis, and then to drop off another sample container for analysis. In this approach, the analyzer is idle during the time that the robot is retuning the analyzed microplate and bringing the new microplate. As time and the number of sample containers analyzed increases, the total down time due to robotic transport may become quite significant.

Another way to increase speed and analytical flexibility problem is to permit manual or automated feeding of sample containers. Unfortunately, switching between manual and automated feeding modes with current analyzers has a number of shortcomings. For example, automated microplate feeding systems may not permit manual feeding while the automated feeder is connected to the analyzer. To use such an analyzer in a manual mode, the automatic feeder must be disconnected.

SUMMARY OF THE INVENTION

The present invention addresses these and other shortcomings by providing a sample feeder that includes (1) a first station that receives and initiates transport of a sample container into an analyzer for analysis, (2) a second station where the sample container is handed off to a transporter that carries the sample container to and from an examination site inside the analyzer, and (3) a third station that collects the sample container after examination. The sample feeder may include a singulation mechanism positioned at the first station and configured to separate a sample container from a stack of sample containers for transport to the analyzer, and/or a stacking mechanism positioned at the third station and configured to add a sample container to a stack of sample containers. The sample feeder further may include a preprocessing bin positioned at the first station for holding a stack of sample containers to be analyzed, and/or a postprocessing bin positioned at the third station for holding a stack of sample containers after they have been analyzed.

The invention also provides a sample feeder that includes (1) a lifter configured to raise or lower a sample container relative to the bottom of a stack of sample containers, and (2) at least one latch having a pick portion, the latch being mounted so that the pick portion moves in and out of gaps between adjacently stacked sample containers in response to up and down movement of the lifter. The lifter and latch may be designed to remove a single sample container from the bottom of a stack of sample containers, or to add a single sample container to the bottom of a stack of sample containers. The latch may include a pick portion that is urged toward the bottom of the stack by gravity, a spring, or other mechanisms.

The invention also provides a sample feeder that includes (1) a lifter configured to impart a raising or lowering motion to a sample container to transfer the sample container to or from a stack of sample containers, and (2) a drive motor configured to generate a driving motion, wherein the lifter includes a cam operatively connected to the drive motor and configured to convert the driving motion into the raising or lowering motion.

The invention also provides an automated analyzer system that includes (1) an analyzer unit having an internal examination site, and (2) first and second external loading stations, the first external loading station configured to receive a sample container before analysis, the second external loading station configured to receive the sample container after analysis. The automated analyzer system may include a robot programmed to deliver a sample container to the first external loading station, and to retrieve a different sample container from the second loading station in the same trip.

The invention will be understood more readily after consideration of the drawings and the detailed description of the invention that follow.

BRIEF DESCRIPTION OF THE FIGURES

FIG. 6 is a perspective view of a sample feeder constructed in accordance with the invention, with bins removed so that internal mechanisms of the sample feeder can be viewed.

DETAILED DESCRIPTION OF THE INVENTION

Figure 1:
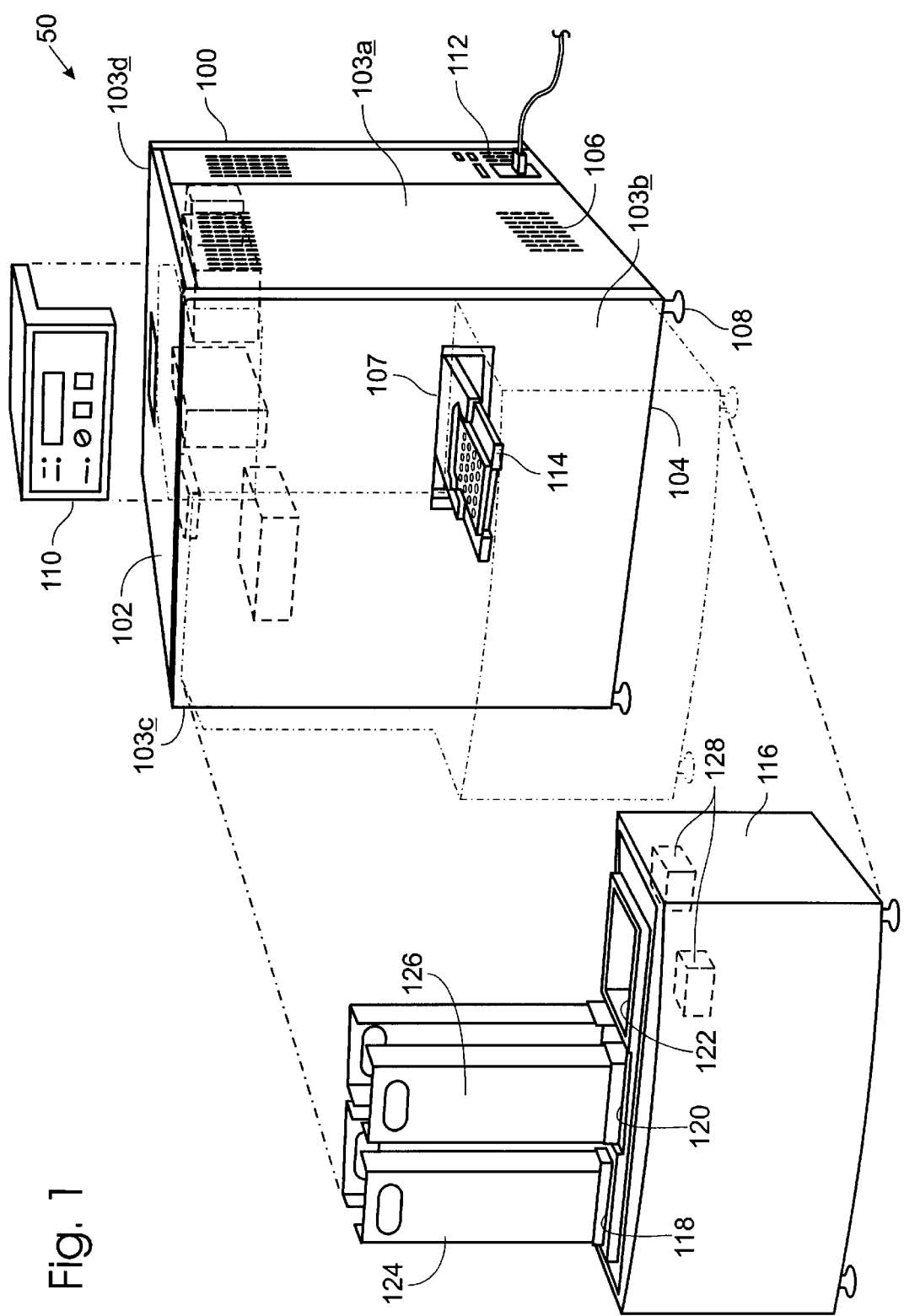
FIG. 1 is a partially exploded perspective view of an analyzer, showing a transporter and sample feeder constructed in accordance with the invention.

FIG. 1 shows a high-throughput luminescence analyzer 50 constructed in accordance with the invention. Components of the analyzer are maintained in a housing 100, both for organization and for protection. Housing 100 is substantially rectangular and includes light-tight exterior top 102, side 103a–d, and bottom walls 104 that reduce background in luminescence measurements. The walls may include vents 106 to facilitate air flow through the analyzer and a transporter port 107 for sample input/output. Housing 100 also may include feet 108 to support the analyzer and to permit air flow between the analyzer and any support structure on which the analyzer is placed.

Analyzer 50 is substantially automated. The analyzer is designed so that user interactions occur primarily through a control unit 110, an electronic input/output panel 112, and a break-out box (not shown), each of which supports a variety of input/output functions. The analyzer also is designed so that sample input/output occurs primarily through a transporter/stage 114 and an optional sample feeder 116.

Transporter 114 generally comprises any device for supporting a sample container. In analyzer 50, transporter 114 moves between the interior and exterior of the analyzer, and may be used alone or together with sample feeder 116 for sample input/output.

Sample feeder 116 generally comprises any device for automatically processing multiple samples. In analyzer 50, sample feeder 116 includes a first (input) station 118 for holding sample containers to be read, a third (output) station 120 for holding sample containers that have been read, and a second (direct transporter access) station 122 for inputting or outputting sample containers that bypasses the input and output stations. Input and output stations 118, 120 accommodate preprocessing and postprocessing sample containers bins 124, 126 that hold and organize stacks of sample containers before and after reading, respectively. Sample feeder 116 also may include a barcode reader 128 for automatically identifying labeled sample containers.

The sample container generally comprises any container for holding at least one sample. Preferred sample containers include microplates. Other suitable sample containers include any sample containers having a shape and rigidity suitable for processing in an analyzer, such as slides or supported gels.

Sample Transporter

FIGS. 2–5 show a stage, which generally comprises any mechanism for supporting a composition in a sample container for analysis by the analyzer. In analyzer 50, the stage includes a transporter 200 and base platform 300.

Figure 2:
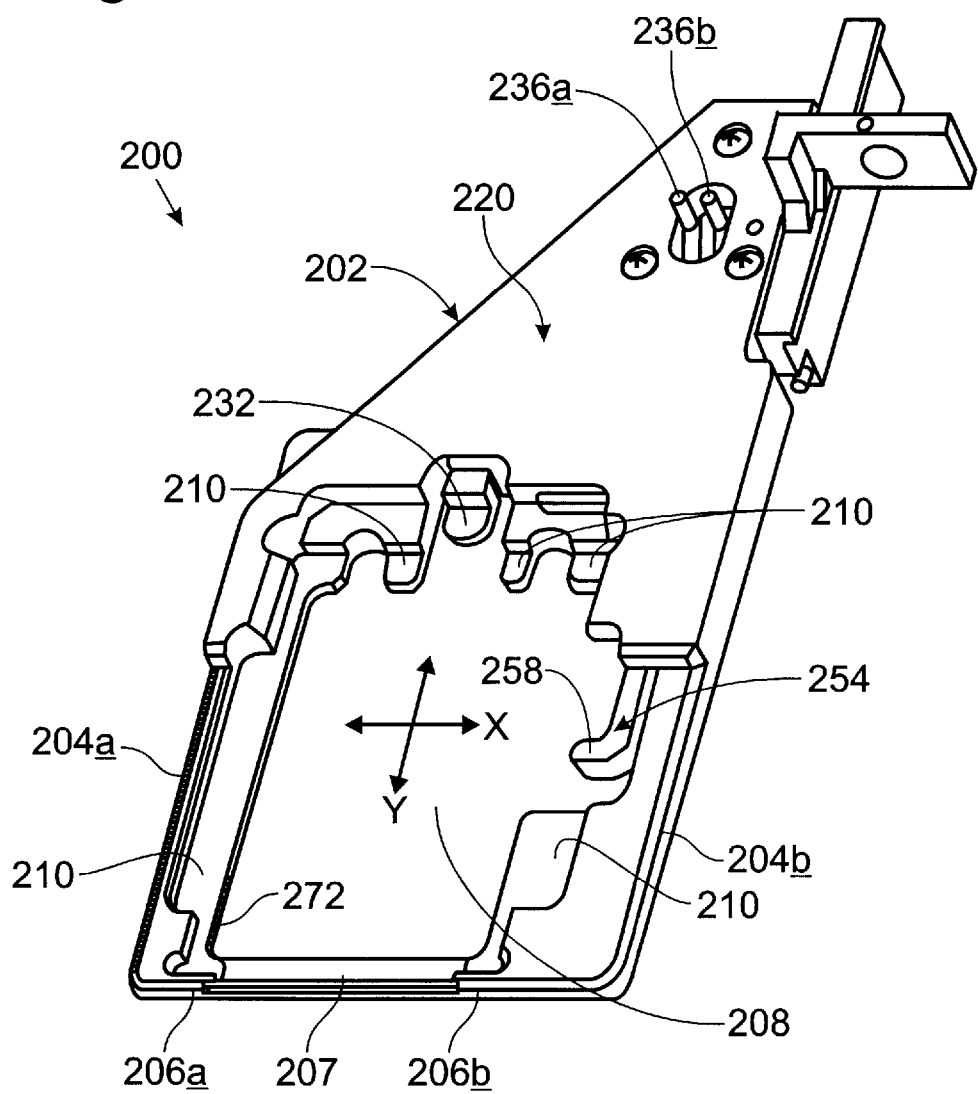
FIG. 2 is a perspective view of the top of a transporter constructed in accordance with the invention.
Figure 3:
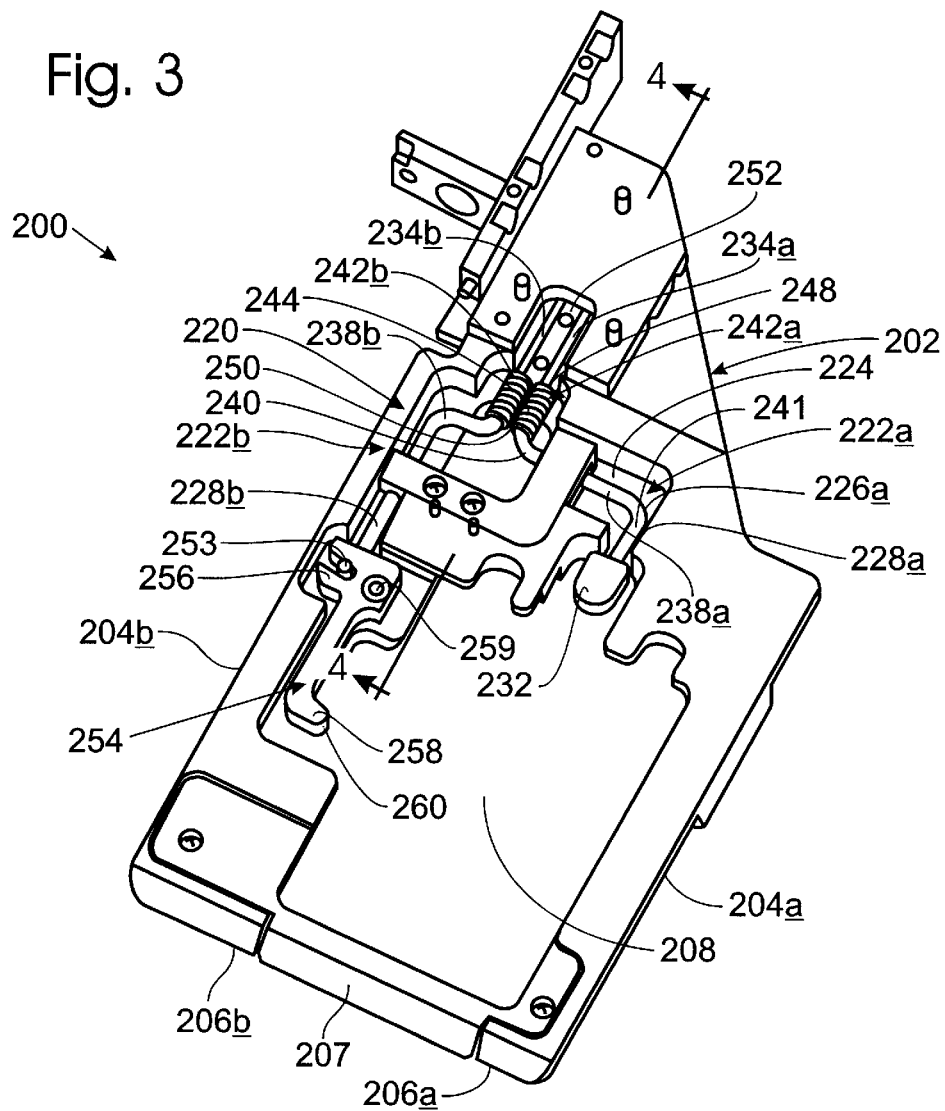
FIG. 3 is a perspective view of the bottom of the transporter shown in FIG. 2.
Figure 4:
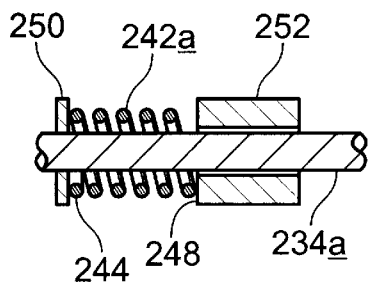
FIG. 4 is a partial cross-sectional view of the transporter shown in FIGS. 2 and 3, taken generally along the line 4—4 in FIG. 3.

FIGS. 2–4 show transporter 200, which includes a transporter body 202 and substantially parallel first and second transporter flanges 204a,b that extend outward from transporter body 202. First and second transporter flanges 204a,b terminate in first and second transporter extensions 206a,b that turn in toward one another without contacting one another. Transporter extensions 206a,b may be joined by a connector portion 207. Transporter body 202, flanges 204a, b, and extensions 206a,b lie substantially in a plane and define a transporter cavity 208 that is larger than the expected peripheral dimension of any sample containers which the transporter is intended to support. The shape of this cavity is chosen to accommodate the shape of the preferred sample containers. In analyzer 50, cavity 208 is generally rectangular to accommodate generally rectangular sample containers, such as microplates. In analyzer 50, long sides of the rectangular sample container are positioned against flanges 204a,b.

Transporter 200 includes a shelf structure and associated frame structure for supporting a microplate or other sample container. For example, transporter shelves 210 along portions of body 202, flanges 204a,b, and extensions 206a,b form a shelf structure that supports the bottom of the sample container. The shelf structure also could include other support mechanisms, such as pins or pegs.

The transporter also includes an automatic sample container positioning mechanism 220 for positioning sample containers precisely and reproducibly within cavity 208. Mechanism 220 includes Y and X axis positioning arms 222*a,b* that contact the sample container to control its Y and X position, respectively. Here, a Y axis is defined as generally parallel to transporter flanges 204*a,b* and an X axis is defined as perpendicular to the Y axis and generally parallel to transporter extensions 206*a,b*. Other coordinate systems also can be defined, so long as they include two noncolinear directions.

Y-axis positioning arm 222*a* lies substantially within a channel 224 in body 202. Y-axis positioning arm 222*a* includes a rod 226*a* which is bent at substantially right angles to form three substantially coplanar and equallengthed segments. A first end segment 228*a* of rod 226*a* terminates near cavity 208 in a bumper 232 for engaging a sample container. A second end segment 234*a* of rod 226*a* terminates away from cavity 208 in an actuator tab 236*a* for controlling movement of arm 222*a*. Actuator tab 236*a* is bent away from body 202. First and second end segments 228*a*, 234*a* are substantially parallel. A middle segment 238*a* of rod 226*a* connects the two end segments at their nontabbed ends 240, 241. An X-axis biasing spring 242*a* having first and second spring ends 244, 248 is slipped over rod 226*a*. First spring end 244 is held to second end segment 234*a* of rod 226*a* by a clamping-type retaining ring 250. Second spring end 248 rests against a rod bearing 252. The Y-axis biasing spring extends substantially parallel to first and second end segments 228*a*, 234*a*. The force from spring 242*a* is transmitted to rod 226*a* by the clamping action of retaining ring 250.

X-axis positioning arm 222*b* also lies substantially within channel 224 in body 202 and is similar to Y-axis positioning arm, except that (1) first end segment 228*b* is longer and middle segment 238*b* is shorter in rod 226*b* of the X-axis positioning arm than in rod 226*a* of the Y-axis positioning arm, (2) first end segment 228*a* terminates in a lever tab 253 in the X-axis positioning arm rather than in bumper 232 in the Y-axis positioning arm, and (3) the two rods bend in opposite directions between first end segments 228*a,b* and second end segments 234*a,b*.

X-axis positioning arm 222*b* is connected via lever tab 253 to an X-axis positioning lever 254 that lies along transporter flange 204*b*. X-axis positioning lever 254 includes first and second lever projections 256, 258 and is pivotally mounted about a lever pivot axis 259 to transporter 200 near the intersection of body 202 and flange 204*b*. First lever projection 256 is substantially perpendicular to flange 204*b* and abuts lever tab 230*b* on X-axis positioning arm 222*b* for actuating the positioning lever. Second lever projection 258 also is substantially perpendicular to flange 204*b* and includes an edge 260 for contacting a sample container.

Transporter 200 functions as follows. For loading, the transporter occupies a loading position substantially outside a housing. In this position, actuator tabs 236*a,b* abut an actuator bar 270, shown in FIG. 5. In addition, biasing springs 242*a,b* are compressed, and bumper 232 and second projection 258 having edge 260 are pulled out of cavity 208. A person, robot, or mechanical stacker then can place a sample container into cavity 208 so that the bottom of the sample container rests on shelves 210. Cavity 208 is larger than the sample container to facilitate this placement and to accommodate variations in sample container size.

In some configurations, connector portion 207 may be removed, such that transporter 200 has an open end. This open end permits a microplate transfer device to enter cavity 208 and the generally rectangular area of the holder. The microplate transfer device may, after moving into the generally rectangular area, move down relative to transporter 200, thereby gently placing the microplate into the generally rectangular area.

For reading, the transporter must deliver the sample container to an examination site inside the housing. In this process, the transporter moves parallel to second end segments 234*a,b*, and actuator tabs 236*a,b* disengage actuator bar 270. Biasing spring 242*a* pushes Y-axis positioning arm 222*a* toward cavity 208. Bumper 232 engages the sample container and pushes it away from body 202 until it abuts extensions 206*a,b*. Biasing spring 242*b* pushes X-axis positioning arm 222*b* toward cavity 208. Edge 260 of second projection 258 engages the sample container and pushes it away from flange 204*b* until it abuts flange 204*a*.

As long as the sample container is placed in any position on the lower guide shelves, it may be positioned (registered) precisely and reproducibly against a reference corner 272 within cavity 208 under the action of both positioning arms. Biasing springs 242*a,b* can be chosen to have different strengths, so that the X-Y positioning action is performed less or more forcefully. In analyzer 50, middle segment 238*b* and first lever projection 256 of positioning lever 254 can be varied in length to cause registration to occur in series, first along the X-axis or first along the Y-axis, and second along the Y-axis or second along the X-axis, respectively. For example, reducing the length of middle segment 238*b* and reducing the length of projection 256 will cause registration to occur first in the X-axis, and second in the Y-axis.

Positioning lever 254 and bumper 232 are retracted when body 202 of the automatic microplate positioning transporter is moved to the eject position by the X,Y stage. Thus, the microplate is placed on transporter shelf 210 only when the lever and bumper are retracted. Two springs 242*a,b* are attached to the rods, which run along the length of the transporter body and end perpendicular to the body. When the transporter is moved to the eject position, the two perpendicular ends of the rods encounter a stop 270, which consists of a rectangular structure located above and parallel to the body. The stop prevents the two perpendicular ends of the actuators, and thus the actuators, from moving with the transporter body. This causes the two springs to contract, changing the position of the transporter arms and increasing the amount of room for the microplate. The microplate then can be placed on the guide shelf of the body. When the body of the automatic microplate positioning transporter is moved back away from the stop, the two perpendicular ends of the actuators no longer are blocked, which allows the actuators, springs, and transporter arms to move into their original position. The expansion of the springs pushes the microplate exactly into position, as defined by the reference corner.

Thus, components of transporter 200 act as first and second releasable clamp mechanisms. The first releasable clamp mechanism applies a force against a first (e.g., Y or X) side of the microplate, thereby securing the microplate in the holder. The second releasable clamp mechanism applies a force against a second (e.g., X or Y) side of the microplate, thereby securing the microplate in the holder from two sides. These clamp mechanisms may sandwich a microplate between the positioning arms and opposing portions of the frame structure, such that the positioning arms function as pushers and the opposing portions of the frame structure function as bumpers for the clamp mechanisms.

The invention provides a method of automatically feeding microplates in and out of an analyzer. The method comprises (1) automatically delivering a microplate just outside an opening to the analyzer, (2) moving a gripping device from inside the analyzer, through the opening, to a location immediately below the microplate; and (3) gently placing the microplate onto the gripping device. The method further may comprise clamping the microplate in the holder by applying a first force against a first side of the microplate, applying a second force against a second side of the microplate, and/or serially performing the clamping steps.

Figure 5:
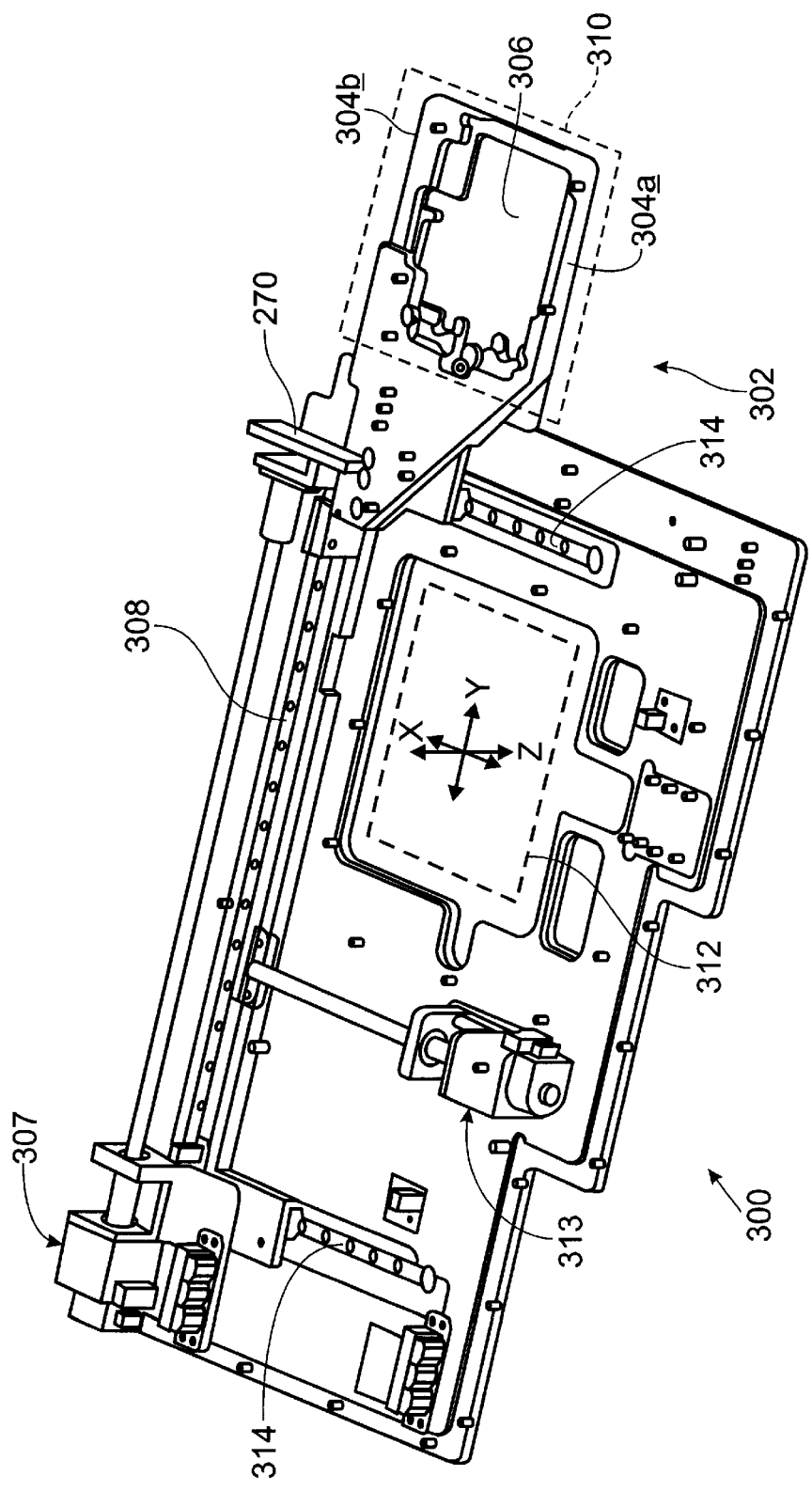
FIG. 5 is a perspective view of a base platform and associated drive mechanisms for moving a transporter along X and Y axes relative to the base platform.

FIG. 5 shows a base platform 300 with drive mechanisms for moving a transporter 302 between loading and examination positions or sites. As previously described, transporter 302 includes flanges 304a,b defining a cavity 306 for receiving and gripping a microplate (not shown). A Y-axis drive mechanism 307 is provided for moving transporter 302 along a first track 308 relative to the Y-axis, from a loading position 310 toward an examination position 312. An X-axis drive mechanism 313 is provided to move transporter 302 to examination position 312 along a second track 314 relative to the X-axis.

In operation, a microplate is loaded in transporter 302 at loading position 310. Transporter 302 is driven toward the examination position by Y-axis drive mechanism 307. A sensor (not shown) detects the presence of the sample container. The analyzer may be configured automatically to read the microplate once the sensor detects its presence, or the analyzer may be configured to signal the system controller through a data port that a microplate has been received and that the analyzer is ready to accept a command to begin reading. The X- and Y-axis drive mechanisms then operate together to align selected microplate wells with an optical axis, substantially parallel to a Z-axis, along which a sensed volume for luminescence detection may be defined by optical components contained in one or both of a top and bottom optics head positioned above and below base platform 300, respectively.

Transporter 300 thus may function both as a sample delivery device in and out of the analyzer, and as a moveable stage for supporting the sample container at the examination site. The cavity in the transporter permits analysis to be carried out from below the holder, when the transporter is functioning as a stage at the examination site.

X- and Y-axis drive mechanisms 307 and 313 may be controlled by a high-performance motion control system that maximizes throughput while minimizing detection errors. A preferred high-performance control system includes precision five-phase stepper motors that employ encoder feedback to move the microplate quickly and accurately to each read position. The control system may optimize the acceleration/deceleration profiles of the microplate to minimize shaking of fluid within the microplate, for example, by minimizing "jerk" (the time rate of change of the acceleration of the microplate). Alternatively, the control system may increase throughput by moving plates more quickly, if higher variation in results due to increased shaking and settling time may be tolerated.

Sample Feeder

FIGS. 6–8 show a sample feeder 400, which generally comprises any mechanism for automatic processing of multiple sample containers. Sample feeder 400 enhances convenience by reducing the amount of human intervention required to run the analyzer. Sample feeder 400 also enhances throughput by reducing the amount of time required to process multiple sample containers.

Generally, sample feeder 400 operates as follows. Before reading, a robot (1) removes a sample container from the bottom of an input stack of sample containers at an input station, (2) transports the sample container to a direct transporter access station, and (3) transfers the sample container to a transporter. After reading, the robot (1) takes the sample container from the transporter, (2) transports the sample container to an output station, and (3) transfers the sample container to the bottom of an output stack of sample containers. Sample feeder 400 requires only two motors to provide these functions with high throughput (~5 seconds for load and unload time).

FIG. 6 shows sample feeder 400 with its preprocessing and postprocessing bins removed, so that internal mechanisms can be viewed. A microplate 402 is loaded from the bottom of a stack of microplates in the input bin into a first (input) station 404. Microplate 402 then is transported on a tray (not shown) to a second (direct transporter access) station 406, where the microplate is handed off to a transporter (not shown). The transporter transports microplate 402 generally along an axis 408 to an examination site inside the analyzer. After analysis, the transporter transports microplate 402 back along axis 408 generally in the opposite direction to second station 406. Microplate 402 then is handed back to the tray, and transported to a third (output) station 410, where the microplate is added to the bottom of a stack of microplates in an output bin.

In analyzer 50, a first linear path defined by axis 408 connects the examination site to the second station, and a second linear path connects the first, second, and third stations, wherein the first linear path is substantially perpendicular to the second linear path. However, analyzer 50 also may have other configurations. For example, the examination site and the first, second, and third stations may all be positioned along a single substantially linear path.

In input station 404, a combination of two lifters and four latches cooperate to singulate or pick a single microplate from the bottom of a stack. (These lifters are concealed by microplate 402 in FIG. 6.) Latches 412 have pick portions that extend into the cavity of first station 404 and support a stack of microplates. Latches 412 are disposed toward the microplates by configuring the latch to have a center of gravity above and inward relative to a pivot point. As the lifters are raised in the input station, the pick portions of the latches are pushed out of the way, so that the microplate can be supported and lowered by the lifters. After one microplate has passed below the latch, latches 412 move back into a supporting position relative to the remainder of the stack.

In output station 410, a different latch configuration is employed. Latches 414 are urged inward toward the microplates by a spring (not shown). When lifter 416 lifts a microplate against latches 414, the microplate pushes the latches out of the way. After one microplate has passed above the latch, latches 414 move back into a supporting position relative to the remainder of the stack.

Figure 7A:
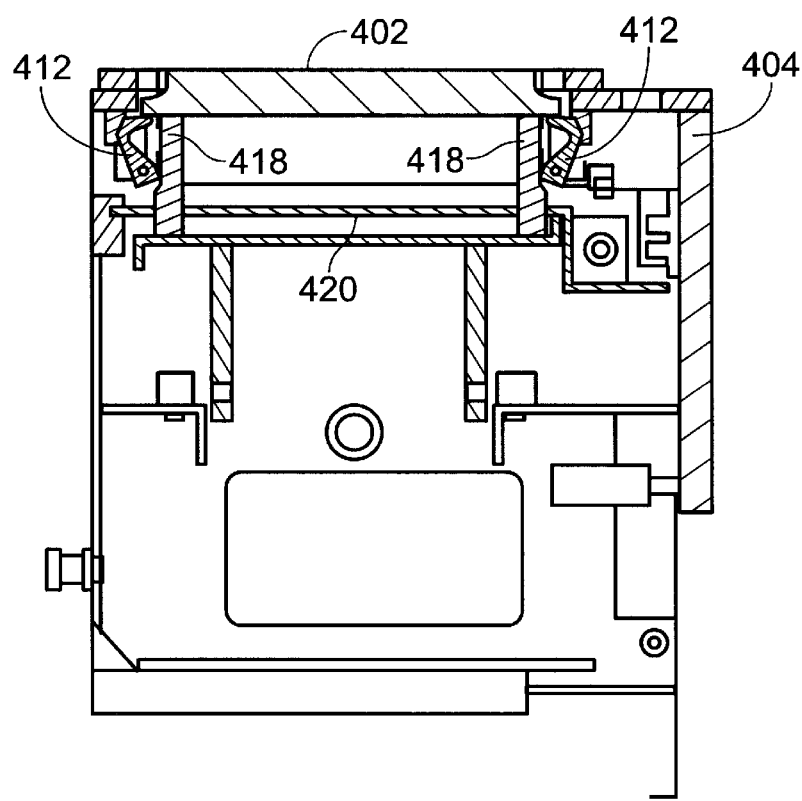
FIGS. 7A and 7B are cross-sectional views through a first (input) station of the sample feeder shown in FIG. 6, taken generally along the line 7AB—7AB in FIG. 6 and showing latch and lifter cooperation to remove a microplate from the bottom of a stack.
Figure 7B:
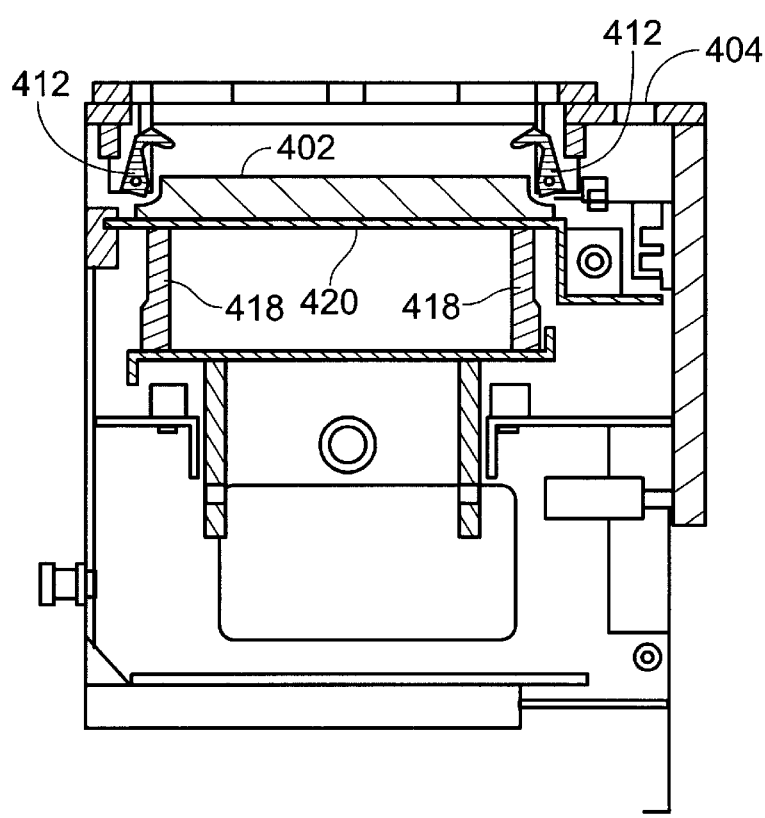

FIGS. 7A and 7B show how input station 404 operates. FIG. 7A shows microplate 402 as it is being picked up at input station 404 prior to analysis. Lifters 418 have moved up through holes in tray 420 to contact the bottom of microplate 402, and in the process have pushed latches 412 out of the way. FIG. 7B shows the same structures as FIG. 7A, except that lifters 418 have dropped, thereby lowering microplate 402 onto tray 420 for transport to the analyzer. Pick portions of latches 412 have moved back into the cavity to support the remainder of the stack.

Figure 8A:
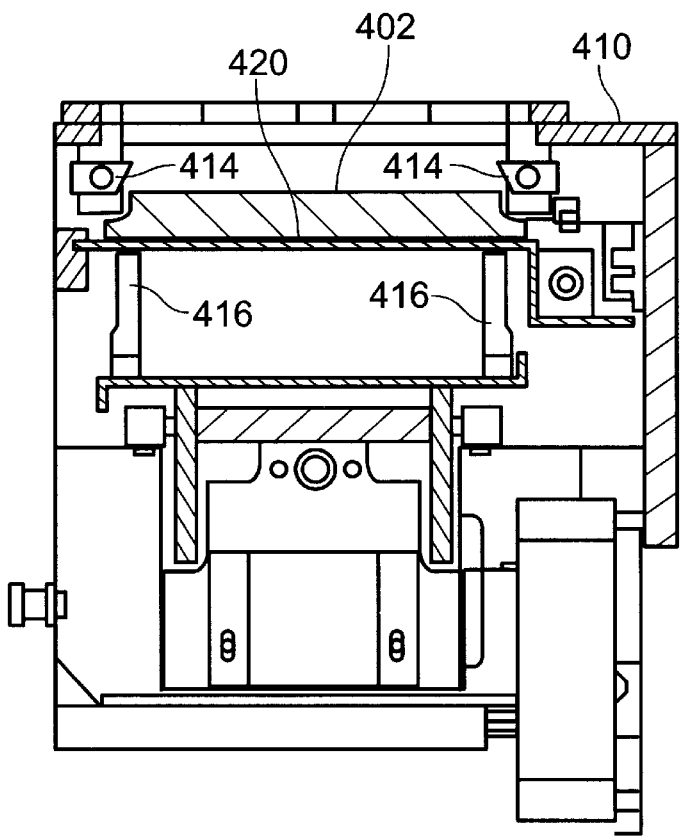
FIGS. 8A and 8B are cross-sectional views through a third (output) station of the sample feeder shown in FIG. 6, taken generally along the line 8AB—8AB in FIG. 6 and showing latch and lifter cooperation to add a microplate to the bottom of a stack.
Figure 8B:
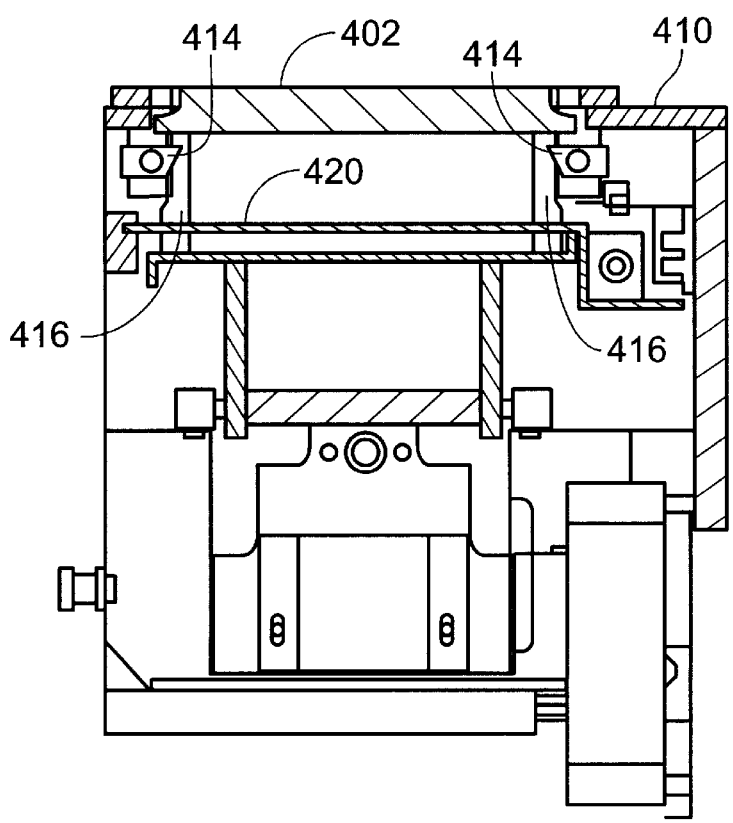

FIGS. 8A and 8B show how output station 410 operates. FIG. 8A shows microplate 402 after it has been delivered to output station 410 following analysis. Lifters 416 then move through holes in tray 420 to raise microplate 402 toward a stack of microplates in the output bin (not shown). FIG. 8B shows the same structures as FIG. 8A, except that lifters 416 have raised microplate 402 past latches 414. Latches 414 are spring biased toward the cavity of third station 410. As lifters 416 raise microplate 402, latches 414 are pushed out of the way by the outer contour of microplate 402. Once microplate 402 is above latches 414, the latches return to their inward position to support the stack of microplates in the output bin. Lifters 416 then retreat downward completely out of the holes in tray 420, so that the tray can translate back to input station 404 to collect another microplate for delivery to the analyzer.

Figure 9:
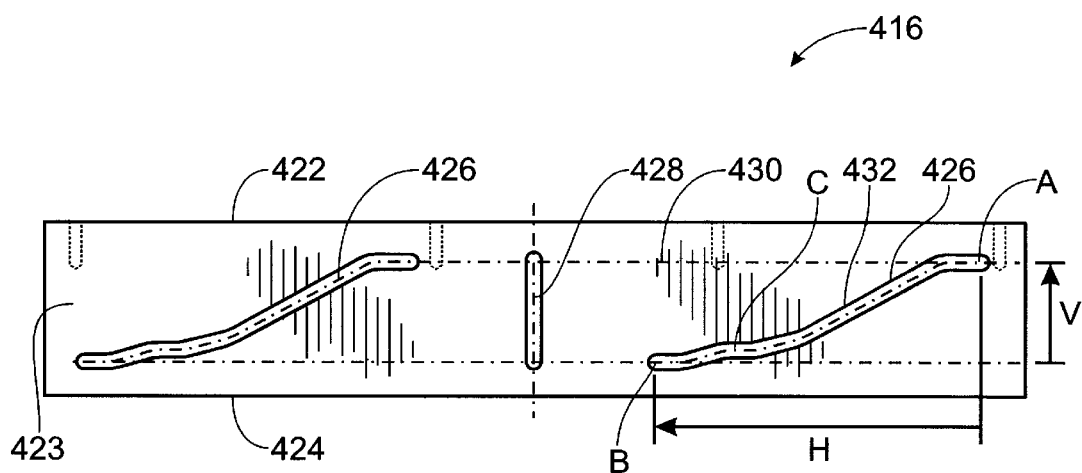
FIG. 9 is a side elevation view of a lifter from the sample feeder shown in FIG. 6.

FIG. 9 shows how lifter 416 operates. Generally, the lifter comprises any mechanism configured to raise or lower a sample container. Lifter 416 is substantially rectangular and includes top 422, side 423, and bottom 424 walls. Each of an opposed pair of side walls 423 includes two sloped drive channels 426, which function as cams, and a vertical guidance channel 428. In sample feeder 400, pins are inserted into drive channels 426 and guide channel 428. In alternative embodiments, pins and channels may be replaced with other components, including ridges, bearings, or rollers. Pins inserted into drive channels 426 are connected to a drive motor, which moves the pins through drive channels 426 between a top position A nearer top wall 422 and a bottom position B nearer bottom wall 424. The pins move horizontally along a line 430, so that the pins push against a side 432 of drive channels 426, urging lifter 416 to move both horizontally and vertically. Pins inserted into guidance channels 428 are connected to relatively fixed portions of sample feeder 400, preventing horizontal motion, but permitting vertical motion, so that lifter 416 only moves vertically. As the pin moves between positions A and B, the pin moves a horizontal distance H and a vertical distance V. It is the vertical displacement that creates the raising and lowering motions. H and V may be optimized for particular sample containers and travel distances; in sample feeder 400, H and V are optimized for microplates and are approximately 10 cm and 3.5 cm, respectively. Lifter 416 is raised when the pin is near position A, and lifter 416 is lowered when the pin is near position B.

In use, the drive motor moves the pins horizontally at a substantially uniform rate; consequently, the slope of drive channel 426 determines the mechanical advantage and the rate of vertical motion. Near positions A, B, and an intermediate position C, the slope of drive channel 426 is substantially zero, so that there is substantially no vertical motion. Stated differently, near positions A, B, and C, a preselected vertical position corresponds to a range of horizontal positions. This configuration makes the vertical position relatively insensitive to motor precision or manufacturing tolerance, because the lifter will be at the same vertical position whenever it simply is near positions A, B, or C. Between positions A and C, and between positions B and C, the slope of drive channel 426 is nonzero, so that there is vertical motion. The slope is largest (approximately 30°) between positions A and C, so that the lifter raises and lowers relatively rapidly when it is farthest from the bottom of the stack of sample containers. The slope is smallest (approximately 15°) between positions B and C, so that the lifter raises and lowers relatively slowly when it is nearest to the bottom of the stack of sample containers.

The drive motor generally comprises any mechanism configured to generate a driving motion. The drive motor used in sample feeder 400 is a stepper motor, which generates a constant torque. Generally, stepper motors and cams provide alternative mechanisms for performing the same function, in this case, generating a varying rate of motion. However, pairing a stepper motor and cam together in the invention provides several advantages. In particular, the cam provides mechanical advantage and positional insensitivity, and permits the stepper motor to be run at a constant, optimal speed. If the stepper motor were used alone, an electronic control system would be necessary to vary raising and lowering speed. Conversely, if the cam were used alone, with a nonstepper motor, an electronic control system with feedback control would be necessary to vary raising and lowering speed.

Together, the lifters and latches form a singulation mechanism configured to separate a microplate (or other sample container) from a stack of microplates in the down-stacking or input operation. This mechanism has inherently low sensitivity to the exact size, shape, construction material, and surface finish of the microplate. As described, the invention may include four inwardly sloping, tapered (or angled) latches that cause the stack of microplates to self-center within the microplates input area to accommodate both relatively small and large microplates sizes. Also as described, the invention may include a feature that causes the microplates to drop gently when the singulation mechanism disengages from the edges of the microplates, thus allowing the microplates to drop onto the lifter mechanism support structure, which lowers the microplates to the tray without spilling fluid from the wells.

The down-stacking latches pivot on pins and are actuated by the lifter mechanism so as to retract when the lifter mechanism rises, thereby releasing the bottom microplate from the stack and allowing it to drop softly onto the lifter. When the latches retract, they pivot on their support pins such that their centers of gravity are offset. Consequently, when the lifter mechanism is lowered, the latches will be activated by gravity to return to their nonretracted or extended state, thereby preventing the next microplates in the stack from dropping as the lifter mechanism is lowered. Because the offset in the center of gravity of the latches is only enough to cause them to return to their extended position, they press only very lightly on the edges of the microplate as it drops. Because the ends of the latches are polished smooth, they exert only a small frictional force on the edges of the microplates so as not to cause the microplate to tilt or otherwise hang up as the lifter mechanism is lowered and the microplate is placed on the tray.

Together, the lifters and latches also form a stacking mechanism configured to add a microplate to a stack of microplates. Generally, the up-stacking mechanism resembles the down-stacking mechanism. The lifter mechanism raises the microplate by a fixed amount, thereby causing it to pass by four spring-loaded latches, which retract as the microplate is raised by the lifter. Once the bottom of the microplate is above the top of the latch, the latches are released, and a spring on each latch causes the latch to extend under the microplate. The lifter mechanism then is lowered, causing the microplate to be captured by the now extended latches. The up-stacked microplate thus is added to the bottom of the output stack.

Sample feeder 400 also may employ alternative singulation mechanisms. For example, singulation mechanisms may (1) take microplates from the bottom of the stack in the input station and add microplates to the bottom of the stack in the output station, as above, (2) take microplates from the bottom of the stack in the input station and add microplates to the top of the stack in the output station, (3) take microplates from the top of the stack in the input station and add microplates to the bottom of the stack in the output station, or (4) take microplates from the top of the stack in the input station and add microplates to the top of the stack in the output station.

Sample feeder 400 permits a robot to deliver a sample container to the input station and to retrieve a different sample container from the output station, both in the same trip. This feature is known as "process compression" and reduces robot hand travel in servicing analyzer 50. For example, if there were only one loading station (e.g., the transporter), the robot would have to remove the analyzed microplate before delivering the unanalyzed microplate. Thus, process compression replaces two separate robot movements with one robot movement. Sample feeder 400 may be configured so that the input and output stations can hold a microplate to facilitate process compression.

Sample feeder 400 is designed to be flexible. The input and output stations can accommodate a variety of commercially available microplates and are large enough to allow microplates to be placed in them by a robot or a human hand. Suitable microplates typically have 96 or 384 wells, but other configurations also can be accommodated. The input and output stations also can accommodate a variety of commercially available preprocessing and postprocessing microplate bins for holding a stack of microplates before and after analysis, respectively. Preprocessing bins may be removed from the input station and replaced with another preprocessing bin containing a new stack of microplates with samples to be analyzed. Similarly, postprocessing bins positioned may be removed from the output station and replaced with another postprocessing bin to receive a new stack of microplates with samples that have been analyzed. Microplate bins may be used with other robotics to dispense, wash, and read without restacking microplates. Suitable microplate bins typically can accommodate 0–60 microplates.

Sample feeder 400 also may include a barcode reader, as shown in FIG. 6, which can be used automatically to identify labeled microplates. The barcode reader 434 preferably is positioned in either of two positions adjacent direct transporter access station 406; these positions permit barcode reader 434 to read barcodes mounted on the long edge or the short edge of microplates. Barcodes are read when sample feeder 400 moves the microplate from input station 404 to direct transporter access station 406. Barcodes cannot be read when microplates are delivered directly to the direct transporter access station 406. Barcode reader 434 can be programmed to decode a variety of symbologies, including SPC (EAN, JAN, UPC), Code 39 (3–43 digits), Codabar (3–43 digits), Standard 2 of 5 (3–43 digits), Interleaved 2 of 5 (4–43 digits), Code 93 (5–44 digits), and MSI-Plessey (4–22 digits), among others. Information obtained from the barcode can be used for various purposes. For example, the barcode can be used to name the report file. The barcode also can be used to convey instructions to the analyzer relating to required changes in assay mode or optics configuration.

Accordingly, while the invention has been disclosed in its preferred form, the specific embodiment thereof as disclosed and illustrated herein is not to be considered in a limiting sense, because numerous variations are possible and no single feature, function, or property of the preferred embodiment is essential. The invention is to be defined only by the scope of the issued claims.

We claim:

1. An apparatus for feeding sample containers in and out of an analyzer, the apparatus comprising:

a first station that receives and initiates transport of a sample container into the analyzer for analysis;

a second station where the sample container is handed off to a transporter that carries the sample container to an examination site inside the analyzer and that returns the sample container from the examination site to the second station; and a third station that collects the sample container after examination.

2. The apparatus of claim 1, wherein the sample container is a microplate.

3. The apparatus of claim 2, wherein the microplate includes a plurality of open sample wells.

4. The apparatus of claim 1, wherein the first station includes a singulation mechanism configured to separate the sample container from a stack of sample containers for transport to the analyzer.

5. The apparatus of claim 4, wherein the stack has a top and bottom, the singulation mechanism taking one sample container at a time from the bottom of the stack.

6. The apparatus of claim 4, wherein the stack has a top and a bottom, the singulation mechanism taking one sample container at a time from the top of the stack.

7. The apparatus of claim 4, further comprising a preprocessing bin positioned at the first station for holding the stack, wherein the preprocessing bin can be removed from the first station and replaced with another preprocessing bin containing a new stack of sample containers with samples to be analyzed.

8. The apparatus of claim 1, wherein the third station includes a stacking mechanism configured to add the sample container to a stack of microplates.

9. The apparatus of claim 8, wherein the stack has a top and bottom, the stacking mechanism adding one sample container at a time to the bottom of the stack.

10. The apparatus of claim 8, wherein the stack has a top and a bottom, the stacking mechanism adding one sample container at a time to the top of the stack.

11. The apparatus of claim 8, further comprising a postprocessing bin positioned at the third station for holding the stack, wherein the postprocessing bin can be removed from the third station and replaced with another postprocessing bin to collect a new stack of sample containers with analyzed samples.

12. The apparatus of claim 1, further comprising a tray that carries the sample container between stations.

13. The apparatus of claim 12, further comprising a sample container stacking and destacking device operatively associated with the tray, the stacking and destacking device moving with the tray and being capable of taking a sample container one at a time from a first stack of sample containers at the first station, handing off the sample container to the transporter, which carries the sample container to and from an examination site inside the analyzer, and adding the sample container to a second stack of sample containers at the third station after analysis.

14. The apparatus of claim 13, wherein the stacking and destacking device includes a lifter and a latch that cooperate to remove a sample container from the first stack, and to add a sample container to the second stack.

15. The apparatus of claim 14, wherein the lifter is configured to raise or lower the sample container relative to the bottom of a stack of sample containers, and wherein the latch has a pick portion, the latch being mounted so that the pick portion moves in and out of gaps between adjacently stacked sample containers in response to up and down movement of the lifter.

16. The apparatus of claim 15, wherein the lifter includes a cam configured to vary the rate at which the sample container is raised and lowered.

17. The apparatus of claim 12, wherein the first station has a dedicated first handler that takes a sample container from a first stack of sample containers and deposits the sample container on the tray, the second station has a second handler that hands-off the sample container from the tray to the transporter, which carries the sample container to and from an examination site inside the analyzer, and the third station has a third handler that transfers the sample container from the tray to a second stack of sample containers after analysis.

18. The apparatus of claim 17, wherein each handler at the first and third stations includes a lifter and a latch that cooperate to transfer a sample container to or from a stack.

19. The apparatus of claim 18, wherein the lifter is configured to raise or lower the sample container relative to the bottom of a stack of sample containers, and wherein the latch has a pick portion, the latch being mounted so that the pick portion moves in and out of gaps between adjacently stacked sample containers in response to up and down movement of the lifter.

20. The apparatus of claim 19, wherein the lifter includes a cam configured to vary the rate at which the sample container is raised and lowered.

21. The apparatus of claim 1, wherein a first linear path connects the examination site to the second station, and a second linear path connects the first, second and third stations, the first linear path being substantially perpendicular to the second linear path.

22. The apparatus of claim 21, wherein the transporter carries the sample container from the second station to and from the examination site generally along the first linear path, and further comprising a tray that carries the sample container between the first, second and third stations on the second linear path.

23. The apparatus of claim 1, wherein the examination site and the first, second, and third stations all are positioned along a single substantially linear path.

24. The apparatus of claim 1, further comprising a robot programmed to deliver a sample container to the first station and to retrieve a different sample container from the third station in the same trip.

25. The apparatus of claim 1, wherein the transporter carries the sample container to and from the examination site along a single path.

26. The apparatus of claim 1, wherein the sample container includes a fluid sample.

27. The apparatus of claim 1, wherein the sample container maintains a horizontal orientation during transport to and from the examination site.

* * * * *